(12) United States Patent
McKeown et al.

(10) Patent No.: US 9,914,017 B2
(45) Date of Patent: Mar. 13, 2018

(54) SPORTS MASK SYSTEM

(71) Applicants: Patrick McKeown, County Galway (IE); Teresa McKeown, County Galway (IE)

(72) Inventors: Patrick McKeown, County Galway (IE); Teresa McKeown, County Galway (IE)

(*) Notice: Subject to any disclaimer, the term of this patent is extended or adjusted under 35 U.S.C. 154(b) by 0 days.

(21) Appl. No.: 15/371,461

(22) Filed: Dec. 7, 2016

(65) Prior Publication Data
US 2017/0333749 A1  Nov. 23, 2017

Related U.S. Application Data

(60) Provisional application No. 62/337,376, filed on May 17, 2016.

(51) Int. Cl.
| | |
|---|---|
| *A61B 5/00* | (2006.01) |
| *A61B 5/1455* | (2006.01) |
| *A63B 21/00* | (2006.01) |
| *A63B 21/008* | (2006.01) |
| *A63B 23/18* | (2006.01) |
| *A63B 24/00* | (2006.01) |

(52) U.S. Cl.
CPC .......... *A63B 23/18* (2013.01); *A61B 5/14552* (2013.01); *A61B 5/6803* (2013.01); *A63B 21/00069* (2013.01); *A63B 21/0085* (2013.01); *A63B 21/4003* (2015.10); *A63B 24/0087* (2013.01); *A63B 2230/208* (2013.01)

(58) Field of Classification Search
CPC ................ A63B 23/18; A61M 16/06–16/0694
See application file for complete search history.

(56) References Cited

U.S. PATENT DOCUMENTS

| | | | |
|---|---|---|---|
| 4,549,543 A | 10/1985 | Moon | |
| 4,973,047 A | 11/1990 | Norell | |
| 5,848,589 A * | 12/1998 | Welnetz | A62B 99/00 128/200.24 |
| 6,554,746 B1 | 4/2003 | Mcconnell et al. | |
| 9,707,444 B1 * | 7/2017 | Danford | A63B 23/18 |
| 2013/0319420 A1 | 12/2013 | Danford | |

(Continued)

OTHER PUBLICATIONS

Phantom Athletics, Home Page, Internet Archive page dated Apr. 7, 2016, https://web-beta.archive.org/web/20160407173529/http://www.phantom-trainingmask.com:80/en.*

(Continued)

*Primary Examiner* — Loan H Thanh
*Assistant Examiner* — Jennifer M Deichl

(57) ABSTRACT

The present invention provides a sports mask for breathing training. The sports mask includes a head assemble containing clips to hold the mask against the head. The sports mask further includes a face band assembly that includes straps that are received by the clips present on the head assembly to hold the face assembly against the face of a user. The face assembly includes a face mask unit comprising an airflow valve. The airflow valve includes an airflow resistance varying module that helps in varying flow of air into the airflow valve. The control of airflow resistance varying module can be either manual or automatic when the mask is connected to a wearable device or a vital parameter collection device.

13 Claims, 16 Drawing Sheets

(56) References Cited

U.S. PATENT DOCUMENTS

2015/0053206 A1* 2/2015 Seppala ............... A62B 18/025
                                                128/202.27
2016/0074611 A1* 3/2016 Higgins ............ A61M 16/0666
                                                128/206.24
2016/0120462 A1* 5/2016 Tunnell .................. A61B 5/486
                                                  600/532
2016/0136367 A1* 5/2016 Varney ................... A63B 23/18
                                                128/202.13
2016/0331917 A1* 11/2016 Bennett ................. A63B 23/18

OTHER PUBLICATIONS

Phantom Athletics, "All about the mask", Internet Archive page dated Apr. 7, 2016, https://web-beta.archive.org/web/20160322212856/http://www.phantom-trainingmask.com:80/en/phantom-trainingmask.*

* cited by examiner

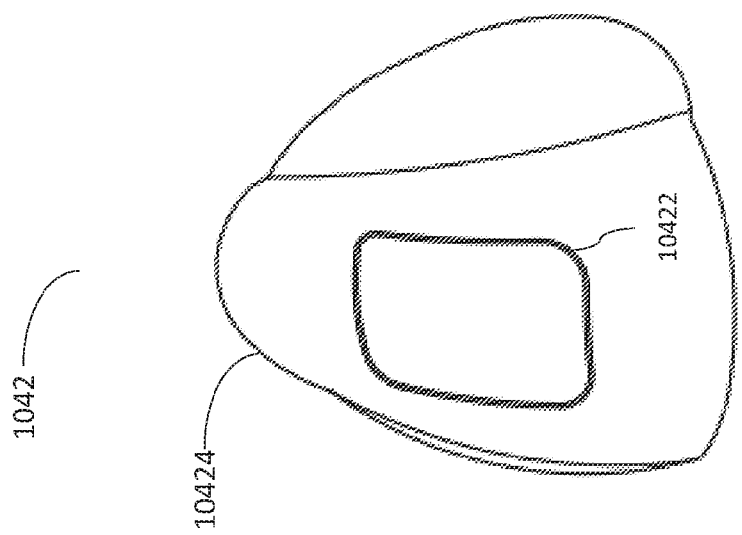

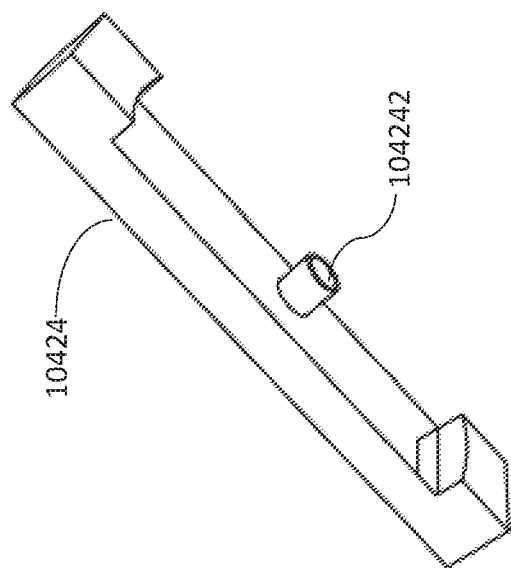

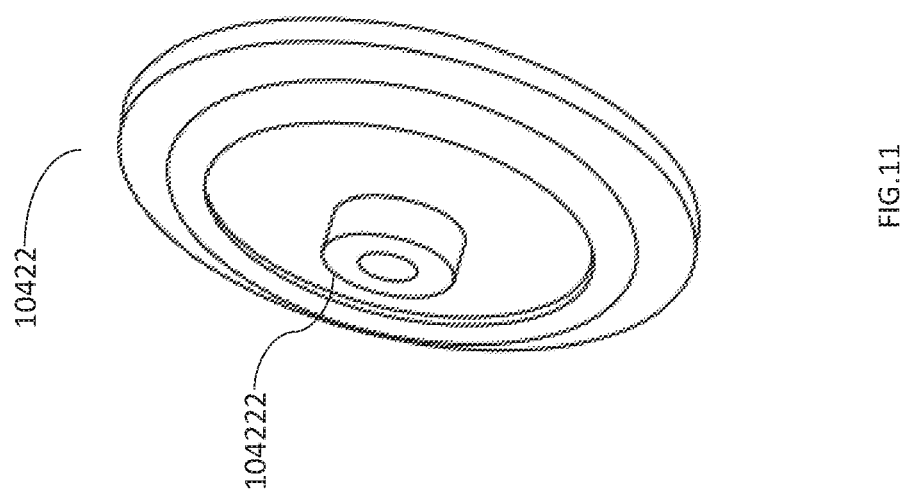

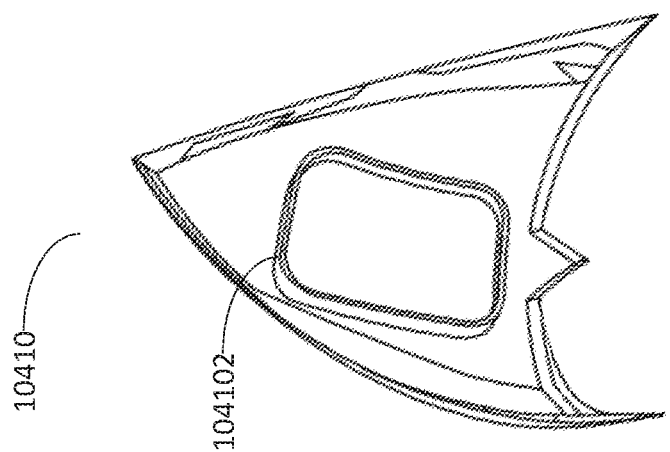

SPORTS MASK SYSTEM

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever 37 CFR1.71(d).

TECHNICAL FIELD

The present disclosure relates to sports mask and more particularly the disclosure relates to a sports mask for adjusting inhalation resistance settings to a user. As the user exercises, resistance settings of the sports mask can be varied based on the level of exertion of the user or blood oxygen saturation level of the user. Restricting air intake during physical exercise can provide the respiratory muscles with an extra load, which in turn works the pulmonary muscles more intensely to strengthen them. Persons with breathing difficulties including asthma, athletes and healthy persons can improve respiratory muscle strength by breathing against resistance.

BACKGROUND

Respiratory muscle training is an essential training for athletes wishing to compete at a high level Respiratory muscle training helps athletes to prepare and get ready for high exertion programs. Restricting air intake during physical exercise can provide the respiratory muscles with an extra load, which in turn works the pulmonary muscles more intensely to strengthen them. Another function of the mask is to pool carbon dioxide during breathing, part of which is inhaled into the lungs to condition the respiratory center in the brain to a higher tolerance of carbon dioxide. This in turn reduces breathlessness during physical activity. Persons with breathing difficulties including asthma, athletes and healthy persons can improve respiratory muscle strength by breathing against resistance.

The treatment is achievable with the aid of masks which have been designed particularly for this function and which include a check valve that allows air to be inhaled with resistance whereas, little or no resistance is provided while the air is being exhaled.

Some of such masks include mask disclosed in U.S. Pat. No. 6,554,746, to McConnell et al discloses an inspiratory muscle training device including an opening for the passage of air to be both inhaled and exhaled and an inlet permitting air to be inhaled to enter the chamber and to pass through the opening. There is provided an adjustable valve to vary the resistance to inhaling. U.S. Pat. No. 4,973,047, to Norell, discloses a therapeutic device for lung exercise which requires a mouthpiece, and has a rotatably adjustable air intake valve. U.S. Pat. No. 4,549,543, to Moon, discloses an air filtering face mask and the concept of a flexible face piece which conforms to the shape of the face of the wearer, and is held in place by scraps or a harness device.

However, the prior art provide separate passages for inhaling and exhaling, which may be worn by a user, in intensely vigorous exercise, without impeding the nature of the exercise conducted. Also, since the masks have manually adjustable valves and, since there is no way that the breathing restrictions could be correlated with the breathing restrictions, hence the breathing training cannot reach an optimum level.

Therefore, an improvement is required on existing masks to optimize the inhalation training for athletes and healing of other ailments as discussed above.

SUMMARY

The present invention comprises a breathing exercise apparatus having one or more of the features recited in the appended claims and/or one or more of the following features, which alone or in any combination may comprise patentable subject matter.

Accordingly, in an embodiment of the invention, there is provided a sports mask. The sports mask includes a head assembly that holds the mask to the head of a user firmly. The mask further contains a face hand assembly that holds a face mask unit to mouth and nose of the user. The face mask unit further contains an air flow valve that helps the user to inhale and exhale during exercise or trainings. This air flow valve furthermore includes an air flow resistance varying module. This module helps to vary flow of air in the air flow valve.

In another embodiment of the invention, there is provided a valve apparatus for a sports mask. The valve apparatus includes a valve grill that helps in protection of the innards of the valve apparatus. The apparatus further includes an airflow valve that is communicatively placed beneath the grill. There is further placed, an airflow cavity, beneath the airflow valve that allows entry and exit of air during breathing event of the user. The apparatus further includes an air flow resistance varying module that further includes a slider. The movement of the slider increases or decreases the resistance of air flow.

In yet another embodiment of the invention is provided a sports mask. The sports mask includes a head assembly that holds the mask to the head of a user firmly. The mask further contains a face band assembly that holds a face mask unit to mouth and nose of the user. The face mask unit further contains an air flow valve that helps the user to inhale and exhale during exercise or trainings. This air flow valve furthermore includes an air flow resistance varying module. This module helps to vary inflow of air in the air flow valve that varies according to the movement of the air resistance varying module. The sports mark further includes a vital parameter measuring device that is communicatively connected to the air flow resistance varying module. The vital parameter measuring device measure real time vital parameters of the user and based on the values of the vital parameters varies the position of the air flow resistance varying module that in turn increases or decreases resistance to inflow of air of the user.

Additional features and advantages are realized through the techniques of the present disclosure. Other embodiments and aspects of the present disclosure are described in detail herein and are considered a part of the present disclosure. For a better understanding of the present disclosure with advantages and features, refer to the description and to the drawings.

BRIEF DESCRIPTION OF THE DRAWINGS

The foregoing summary, as well as the following detailed description of various embodiments, is better understood when read in conjunction with the drawings provided herein. For the purposes of illustration, there is shown in the drawings exemplary embodiments; however, the presently disclosed subject matter is not limited to the specific methods and instrumentalities disclosed.

FIG. 6 illustrates a line diagram depicting innermost unit of the face mask unit of the face assembly, in accordance with an embodiment of the invention.

FIG. 10 illustrates a line diagram depicting a valve catcher, in accordance with an embodiment of the invention.

FIG. 11 illustrates a line diagram depicting a valve, in accordance with an embodiment of the invention.

FIG. 12 illustrates line diagram depicting a grill cover, in accordance with an embodiment of the invention.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 1:
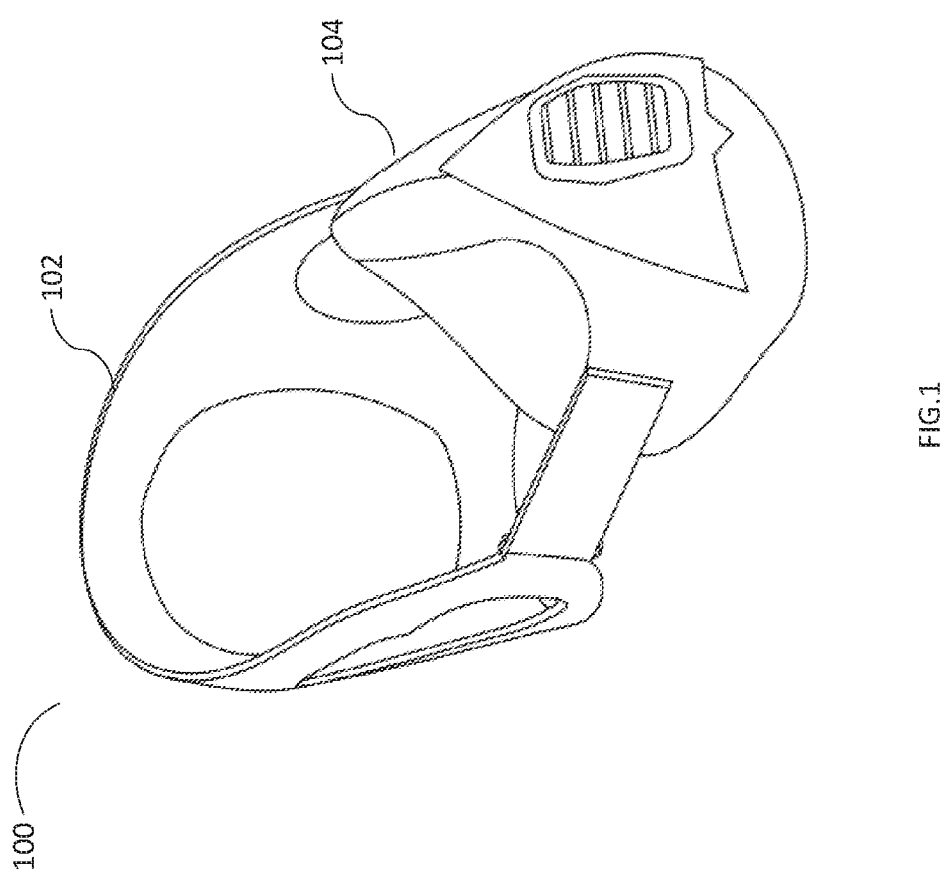
FIG. 1 illustrates a line diagram depicting a sports mask, in accordance to an embodiment of the invention.

Referring now to FIG. 1, a line diagram that depicts a sports mask 100, in accordance with an embodiment of the invention. The sports mask includes a head assembly 102 that helps in keeping the sports mask 100 fixed to head of a user. The head assembly 102 is linked to a face assembly 104. Details of head assembly 102 and face assembly 104 will be discussed in detail in subsequent figures. In an embodiment of the invention, the sports mask 100 may include a connecting button (not shown) to initiate a connection with a wearable device. Details of the embodiment will be described later.

Figure 2:
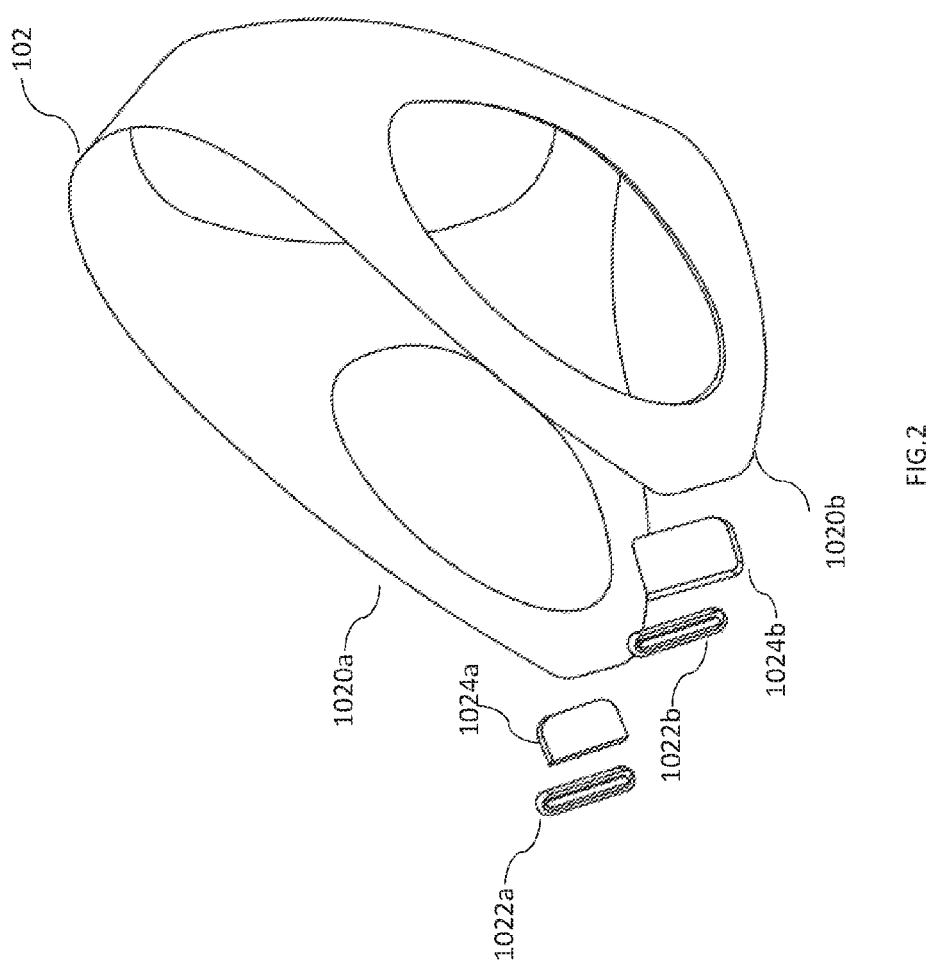
FIG. 2 illustrates a line diagram depicting head assembly and various parts, in accordance to another embodiment of the invention.

Now, referring to FIG. 2, that depicts a head assembly 102 and its various constituent parts. The head assembly, as described keeps the sports mask fixed to the head of the user. In an embodiment of the invention, the head assembly 102 is made up of durable, and stretchable fabric material. However, there can be other materials as well that may be utilized like fiber, plastic etc. Head assembly 102 includes a left strip 102a and a right strip 102b. Each of the strips 1020a and 1020b further includes a locking clip 1022a and 1022b joined to the strips 1020a and 1020b by joining patches 1024a, and 1024b. The clips 1022a and 1022b, may be made up of metal, plastic, fiber, etc. The clips 1022a, and 1022b are utilized to receive the face assembly 104 and place it firmly on mouth and nose of the user. Details of the face assembly 104 will be discussed in detail.

Figure 3:
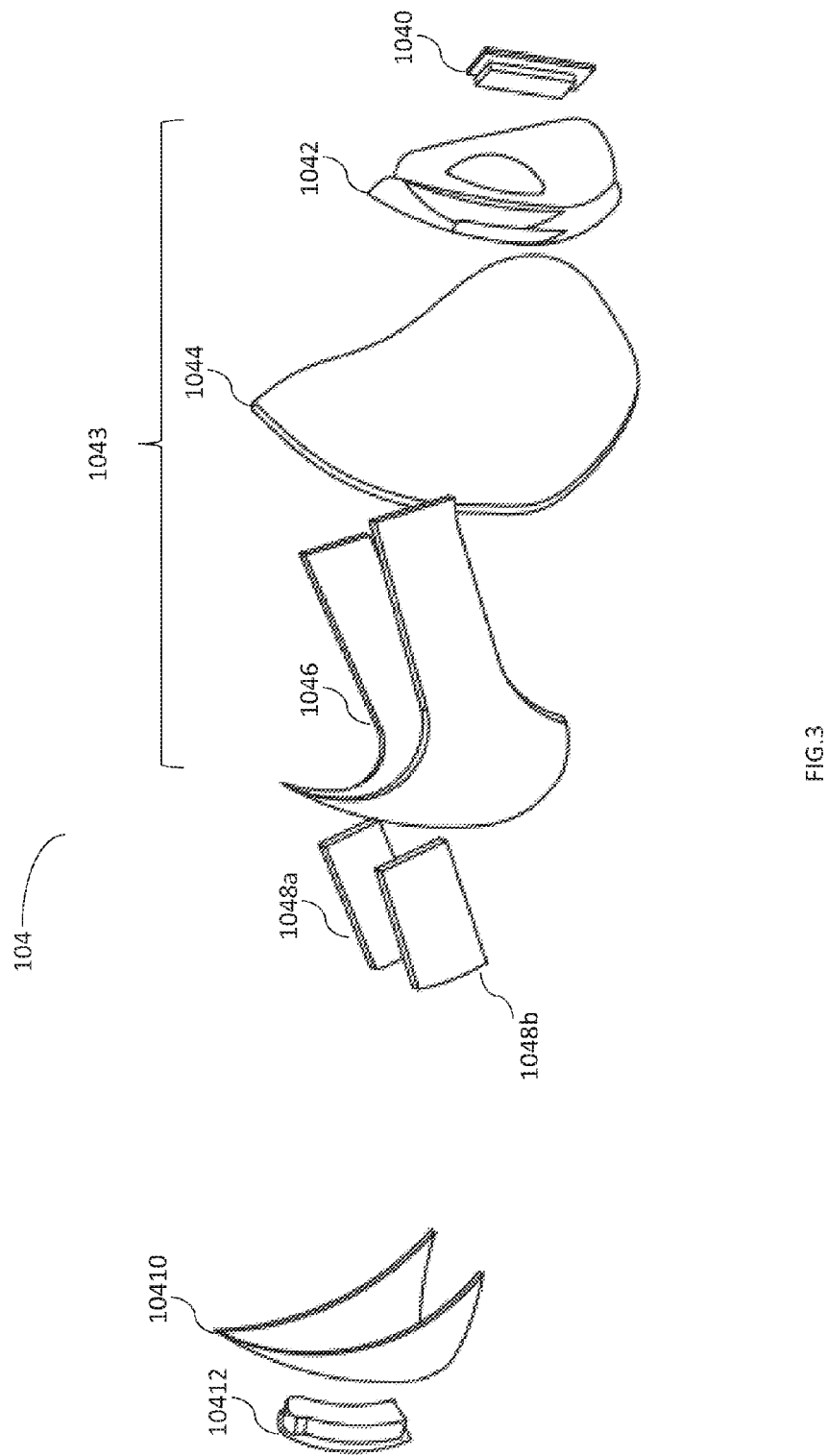
FIG. 3 illustrates a line diagram depicting exploded view of face assembly, in accordance with an embodiment of the invention.

Now, referring to FIG. 3 that depicts a face assembly 104 of the sports mask 100, in accordance with an embodiment of the invention. Face assembly 104 is placed on the mouth and nose region of the user while being used. Face assembly 104 includes various components that will now be discussed in detail. There is present a face mask unit 1043. The face mask unit 1043 is placed within the face assembly 104 to enable inhalation and exhalation of air by the user. The face mask unit further contains an outer unit 1046, a middle unit 1044, and an innermost unit 1042. Details of all will be described later.

Still referring to FIG. 3, the face assembly 104, further includes a grill cover 10410. Grill cover 10410 is provided to keep safe and receive a grill 10412. Grill cover 10410 may be made up of plastic, or fiber or any other strong material. The grill cover, as disclosed above receives the grill 10412. Details of the grill 10412 will be received later. The grill cover 10410 with the affixed 10412 is attached to the outer unit 1046 of the face mask unit 1043. The attachment is done through attachment straps 1048a and 1048b. The attachment straps can be either glued or sewn to the outer unit 1046. However, there can be other means of attaching the grill cover to the outer unit 1046. The face assembly 104 further contains an air flow module 1040. The air flow valve assembly 1040 can be fixed to the innermost unit 1042 of the face mask unit 1043 and is finally in communication with the grill 10412 when all the parts are connected to each other. Further details of the module will be explained later.

Figure 4B:
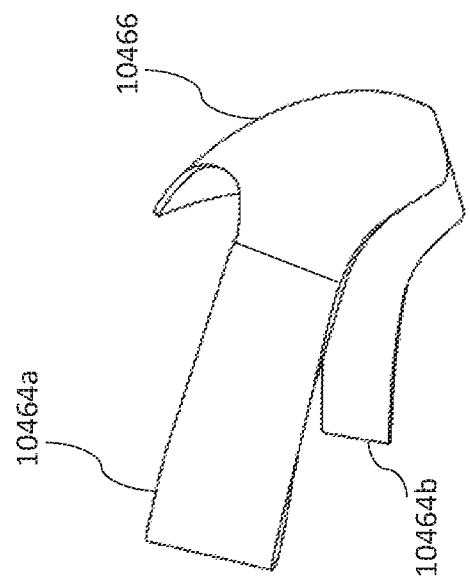
FIG. 4B illustrates a line diagram depicting side view of an outer unit of face mask unit of the face assembly, in accordance with an embodiment of the invention.
Figure 4A:
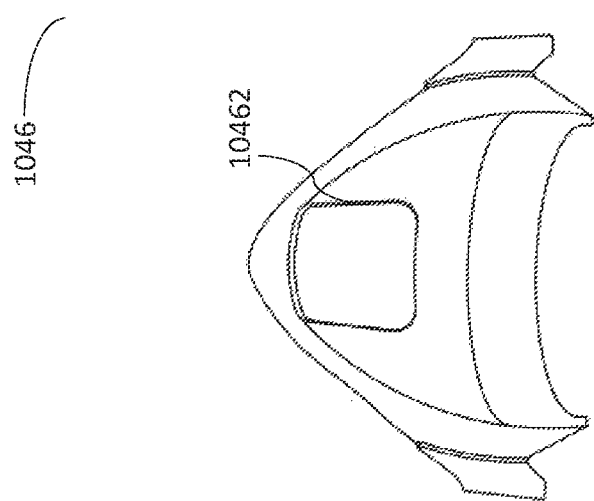
FIG. 4A illustrates a line diagram depicting inner view of an outer unit of face mask unit of the face assembly, in accordance with an embodiment of the invention.

Now referring to FIGS. 4A and 4B that depict inner view and side view respectively of the outer unit 1046 of the face mask unit 1043. The outer unit 1046 includes a left strap 10464*a* and a right strap 10434*b* that are received by the left clip 1022*a* and 1022*b* of the head assembly. This arrangement then places this face mask unit 1043 firmly on the head of the user. The outer unit 1046 also includes a cavity 10462 that is present to place and connect the grill 10412 to the air flow valve assembly 1040. In an embodiment of the invention, the straps 10464*a* and 10464*b* may have Velcro fastener at their ends to tighten or loosen and adjust the placement of the face assembly 104. In other embodiments, the straps 10464*a* and 10464*b* can be flexible and can be permanently fixed to the clips 1022*a* and 1022*b*. The straps 10464*a* and 10464*b* can be fixed to main body 10466 of the mask. The main body 10466 can be made up of, however not limiting the scope of the invention, high grade plastic, fiber, foam, etc.

Figures 5A, 5B:
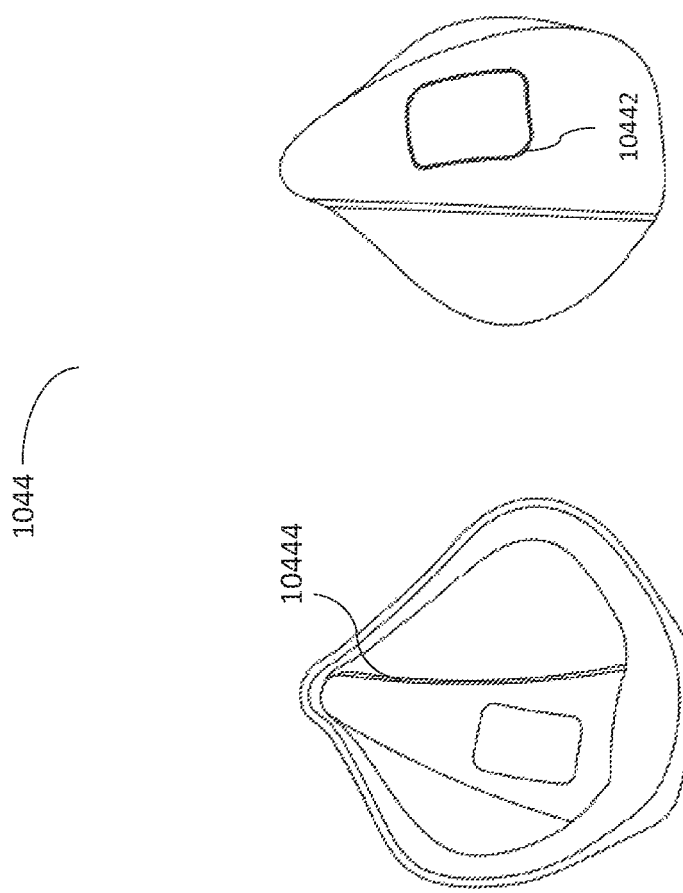
FIG. 5A, illustrates a line diagram depicting inner view of a middle unit of the face mask unit of the face assembly, in accordance with an embodiment of the invention.
FIG. 5B illustrates a line diagram depicting front view of a middle unit of the face mask unit of the face assembly, in accordance with an embodiment of the invention.

Now, further referring to FIG. 5A, 5B depicting inner view and front view respectively of the middle unit 1044 of the face mask unit 1043. The main body 10444 of the middle unit 1044 can be made up of any of a plastic, a fabric, a foam, etc. the middle unit 1044, includes a cavity 10442 that is configured to receive and connect the grill 10412 and the air flow valve assembly 1040.

Now referring to FIG. 6, that illustrates the innermost unit 1042 of the face mask unit 1043. The innermost unit 1042 includes a cavity 10422 for helping the air flow valve assembly 1040 to connect with the grill 10412. The main body 10421 of the innermost unit 1042 is made up of any of a plastic, a foam, and a fabric.

Figure 7:
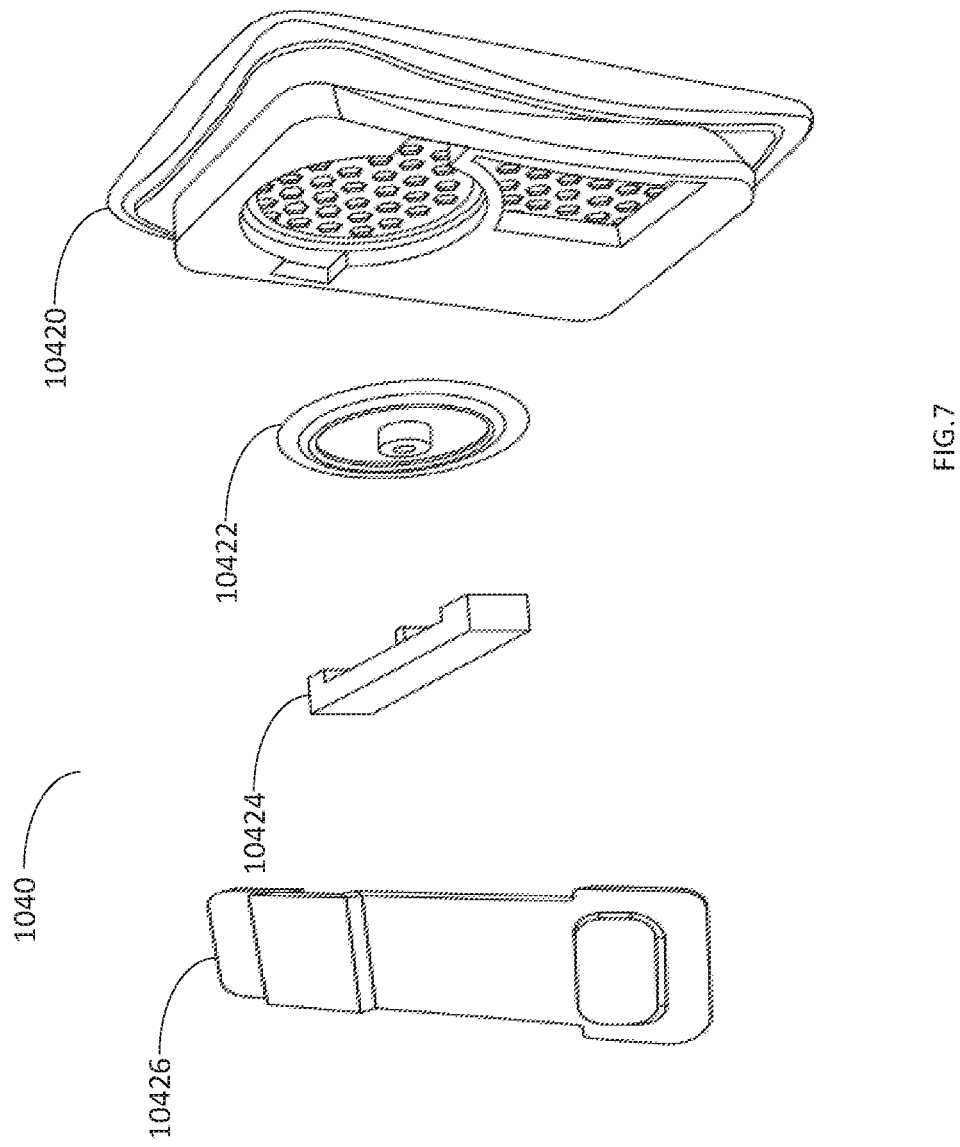
FIG. 7 illustrate a line diagram depicting exploded view of an airflow valve assembly of the face assembly, in accordance with an embodiment of the invention.

Now referring to FIG. 7 that illustrates exploded view of an airflow valve assembly 1040, in accordance with an embodiment of the invention. The airflow valve assembly 1040, includes an airflow vent 10420. This is the innermost unit of the airflow valve assembly 1040. The airflow vent 10420 is in direct communication with nose and mouth of the user. The airflow vent 10420, receives an airflow valve 10422 that is fixed on the airflow vent 10420 using a valve catcher 10424. The airflow valve catcher 10424, fixes the airflow valve 10422 on to the airflow vent 10420. The airflow valve assembly 1040, further includes a slider unit 10426. The slider unit 10426, is connected to the valve catcher 10424 on which the slider unit 10426 may be able to slide. The sliding mechanism can be either manual or automatic. The slider unit 10426, can also be further connected to a motor (not shown in figure) that may help it to slide left or right for opening or closing of the airflow vent 10420. The opening and closing increases or decreases flow of air for the user performing or undergoing training exercise.

Figure 8:
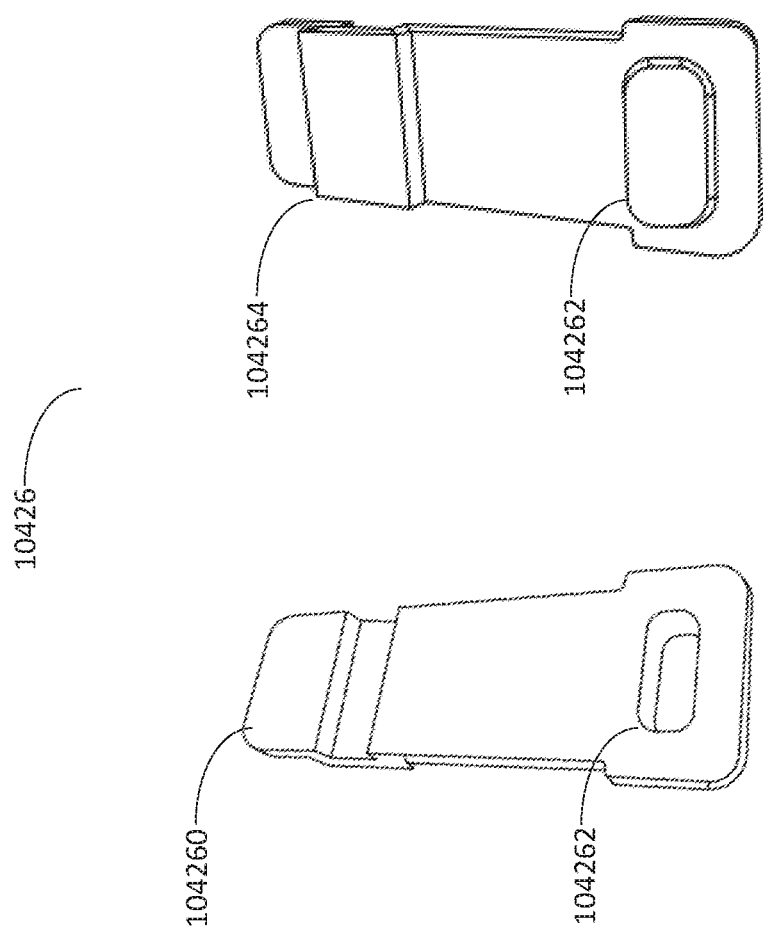
FIG. 8A illustrates a line diagram depicting back side view of a slider unit, in accordance with an embodiment of the invention.
FIG. 8B illustrates a line diagram depicting front view of a slider unit, in accordance with an embodiment of the invention

Now referring to FIGS. 8A and 8A, illustrating back side view and front view respectively of the slider unit 10426. In an embodiment of the invention, slider unit 10426 includes a sliding button 104262 for manually sliding the slider unit 104262. Also, there may be present a sliding notch 104264 that helps in sliding movement. However, in other embodiments the slider unit 104262 can be connected to a small motor (not shown in figure) to facilitate the sliding movement. The slider unit 104262 may be made up of rubber, plastic, or metal.

Figure 9:
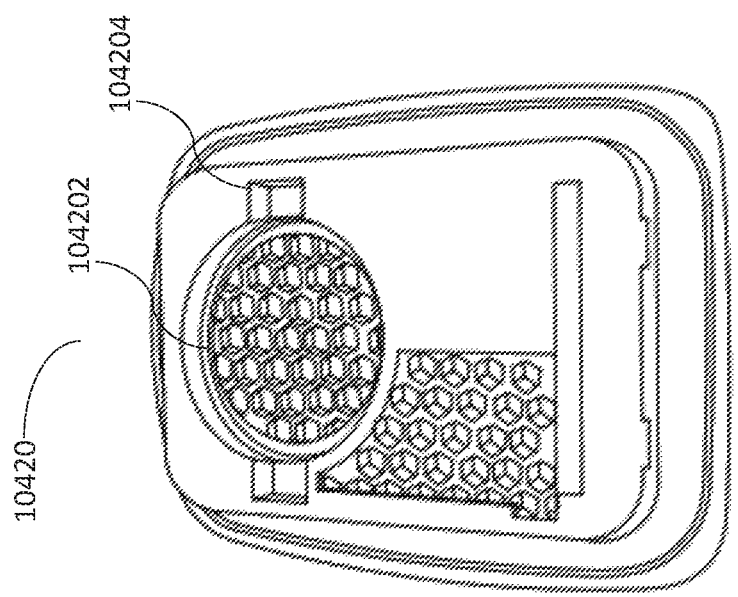
FIG. 9 illustrates a line diagram depicting an airflow vent, in accordance with an embodiment of the invention.

Now referring to FIG. 9, illustrating an airflow vent 10420 that helps in inflow and outflow of air to the user. The airflow vent 10420 includes air holes 104202 in hexagonal form. However, there may be different form factor of holes that may be utilized for the same purpose. The airflow vent 10420 also, includes a valve catcher notch 104204 that receives the valve catcher 10424. It is to be noted that the airflow vent 10420 can have any other different configuration. The present configuration (vertical configuration) of half body of the airflow vent 10420 having air holes 104202 and half body being opaque has been shown for exemplary purposes. In other embodiments, the configuration ca be changed to a horizontal configuration.

Now referring to FIG. 10, illustrates the valve catcher 10424 that includes a catching notch 104242 to fix the valve 10422 on to the airflow vent 10420. The material of the valve catcher can be anyone of a metal, plastic, or fiber, etc.

Now referring to FIG. 11 illustrating the valve 10422 in accordance with an embodiment of the invention. The material of the valve can be a plastic, a rubber, or a foam. It is to be understood that the shape of the valve can be varied as per the design preferences. Here however, for the purposes of example, the shape has been chosen as to be circular. The valve 10422 includes a notch 104222 that receives the catching notch 104242 to fix the valve on to the airflow vent 10420.

Figure 13B:
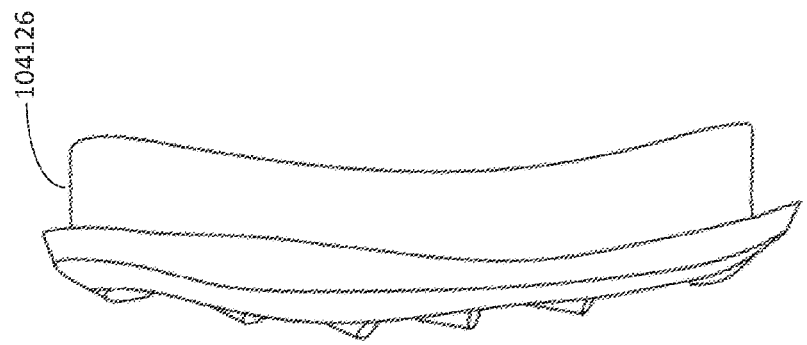
FIG. 13B illustrates a line diagram depicting side view of a grill, in accordance with an embodiment of the invention
Figure 13A:
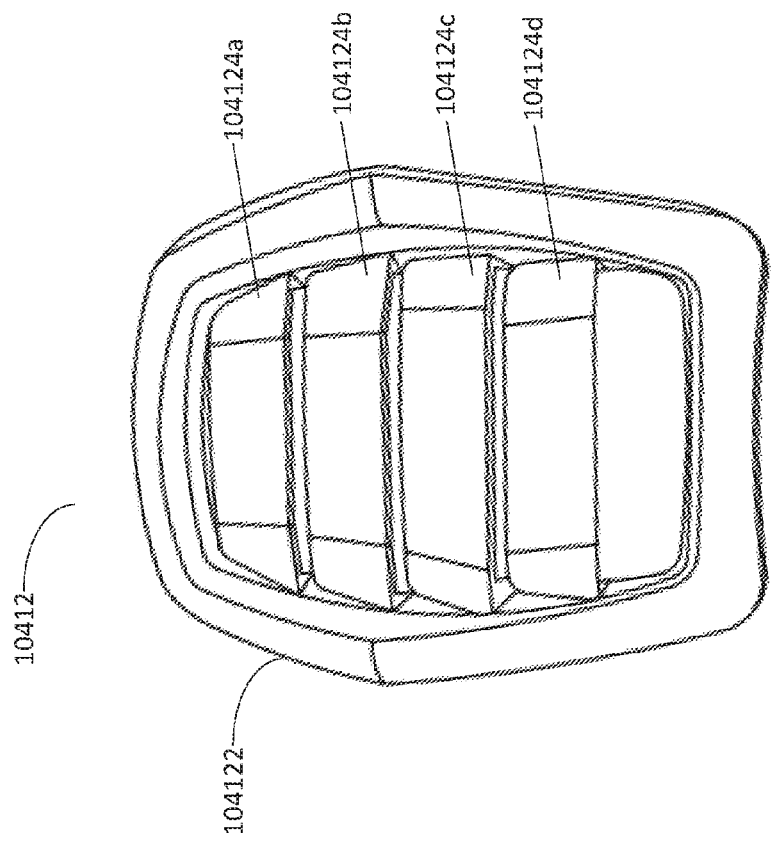
FIG. 13A, illustrates a line diagram depicting front view of a grill, in accordance with an embodiment of the invention.

Now referring to FIG. 12, illustrating the grill cover 10410. The grill cover 10410 can be made up of anyone of a metal, plastic, fiber, foam or a hardened cloth. Grill cover 10410, includes an opening 104102 that facilitates in communication of the airflow assembly 1040 with the grill 10412 as depicted in FIGS. 13A and 13B. FIGS. 13A and 13B illustrate front view and side view respectively of the grill 10412. Grill 10412 includes a side frame 104122. The side frame 104122 can be made up of any one of a metal, a plastic, a rubber, or foam, etc. further, the grill 10412 includes a base frame 104126 (shown in FIG. 13B). The base frame is again made up of anyone of a metal, a plastic, a rubber, or foam, etc. There are also present additional fins 104124*a*-104124*d*, which help in filtering of the air.

Figure 14:
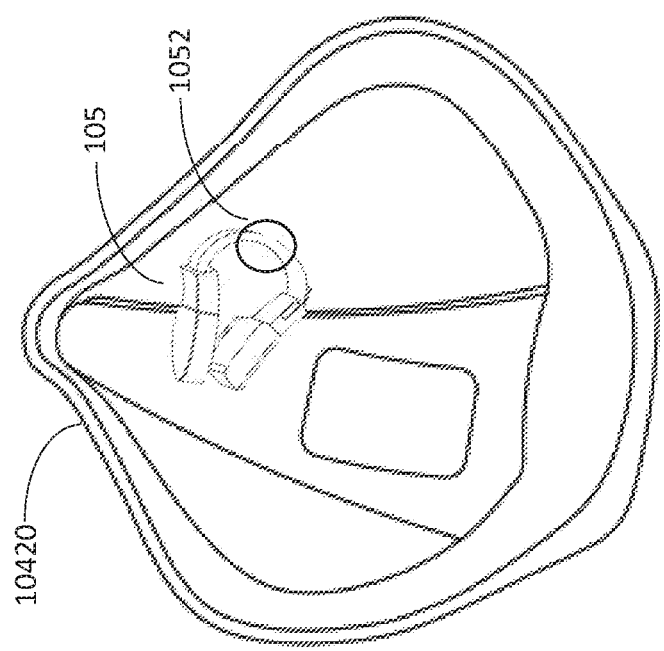
FIG. 14 illustrates line diagram of a vital parameter calculating unit attached to inner side of outer cover of the face assembly, in accordance with an embodiment of the invention.

Now referring to FIG. 14, illustrating a vital parameter collection device 105, attached to the innermost unit 10420 of the face mask unit 1043, in accordance with an embodiment of the invention. In an embodiment of the invention, the vital parameter collection device 105 is a pulse oximeter. Pulse oximeter is a medical device that indirectly monitors the oxygen saturation of a patient's blood (as opposed to measuring oxygen saturation directly through a blood sample) and changes in blood volume in the skin, producing a photoplethysmogram. The pulse oximeter 105 is in direct communication with a microcontroller (not shown in figure) embedded within the face assembly 104. The microcontroller includes stored instructions for various levels blood oxygen saturation readings. Hence, the microcontroller, as per the increased or decreased levels of blood oxygen saturation levels, may control the sliding of the slider unit 10426 by controlling the motor (not shown in figure) to slide. Based on pre-fed instructions, if the blood oxygen level falls below a threshold level, the microcontroller may open the slider unit 10426 to allow more air intake and vice versa.

In other embodiment of the invention, the sports mask may be connected to a wearable device through a network. The wearable device could be a smart watch. The network for communication could be any short range wireless connection like Bluetooth, Wi-Fi, etc. There may be placed a microcontroller placed on the sports mask to collect readings from the pulse oximeter 105 and send these to the wearable device. The sliding function of the slider unit 10426 may also be controlled by the wearable device or smart watch by user's interference or the control can be automatic based on the pre-fed instructions. Based on pre-fed instructions, if the blood oxygen level falls below a threshold level, the microcontroller may open the slider unit 10426 to allow more air intake and vice versa.

Figure 15:
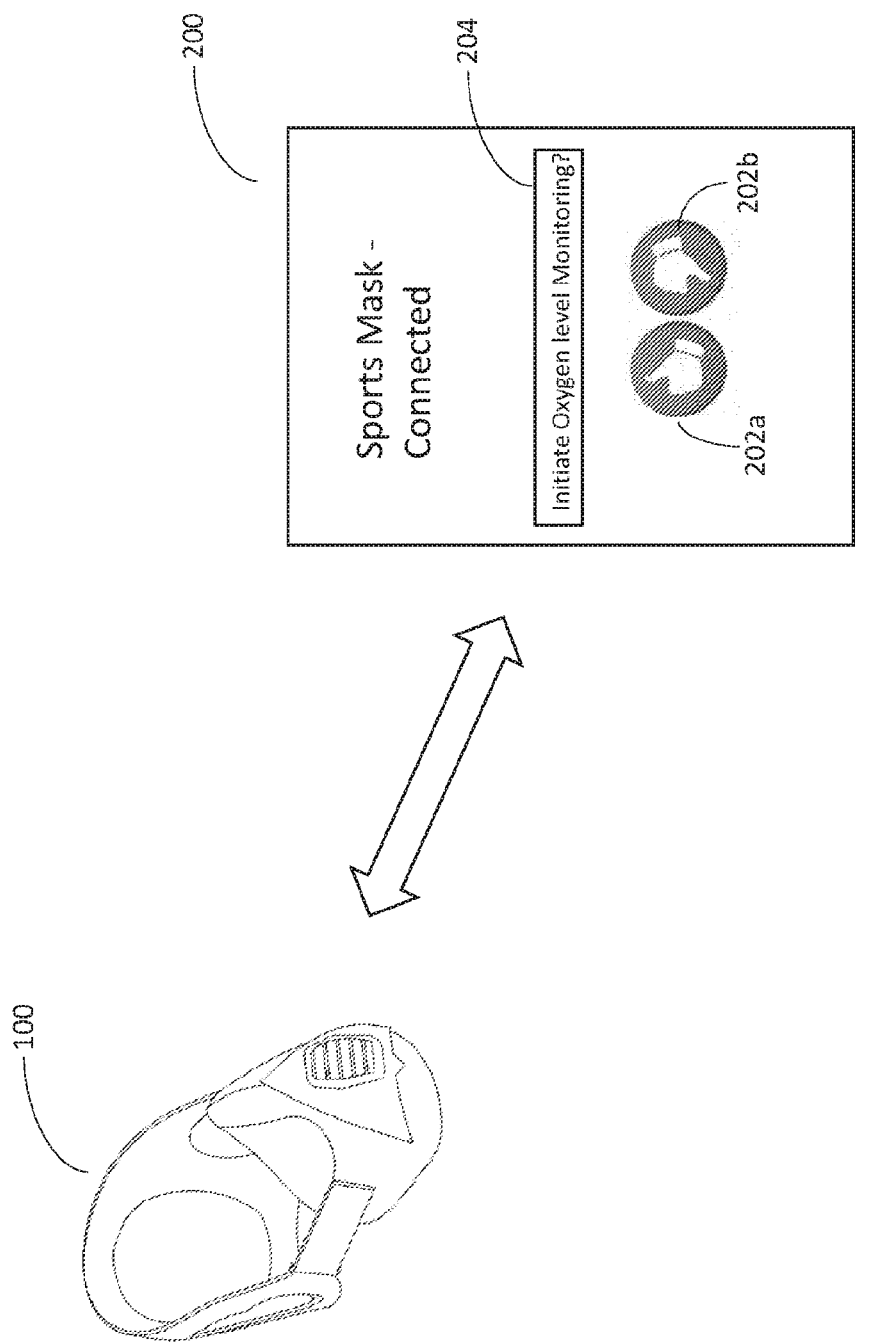
FIG. 15, illustrates a diagram depicting a wearable device connected to sports mask, in accordance to an embodiment of the invention.

Now referring to FIG. 15, illustrating a wearable device 200 connected to the sports mask 100, in accordance with an embodiment of the invention. The sports mask 100 may include a button (not shown in figure) to initiate a connection request to the wearable device 200. The connection can be through any of the small range wireless connections including Wi-Fi, Bluetooth, ZigBee, Near Field Communication (NEC), etc. The connection, once successful, initiates an application launch that may present an interface as shown in the figure. There may be present various icons on the application interface. There may be provided a query field 204 wherein the user is provided with a query "Initiate Oxygen Level Monitoring?" if the user wants to use auto-slide control feature, the user may choose thumbs up icon 202a. On choosing this, the user enables the automatic control of the slider unit 10426. On choosing thumbs down, the user can control the sliding manually.

Figure 16C:
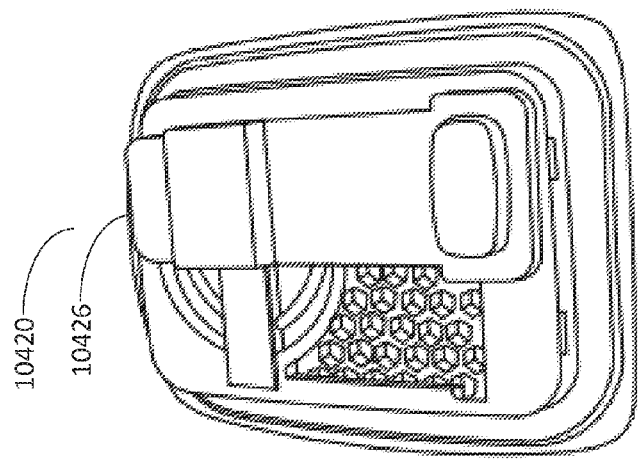
FIG. 16C illustrates a line diagram depicting slider for high intake of air, in accordance with an embodiment of the invention.
Figure 16B:
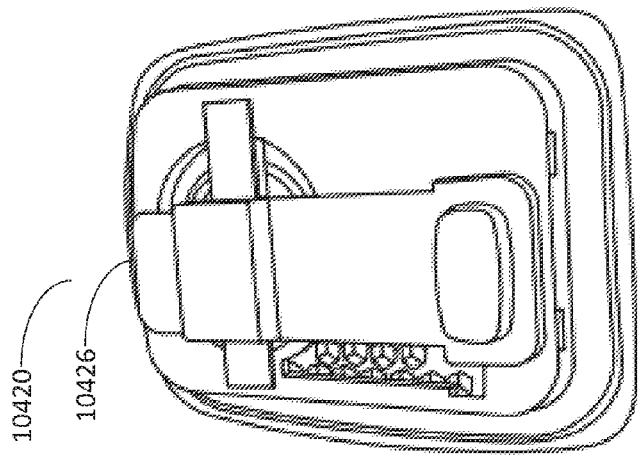
FIG. 16B illustrates a line diagram depicting slider for medium intake of air, in accordance with an embodiment of the invention.
Figure 16A:
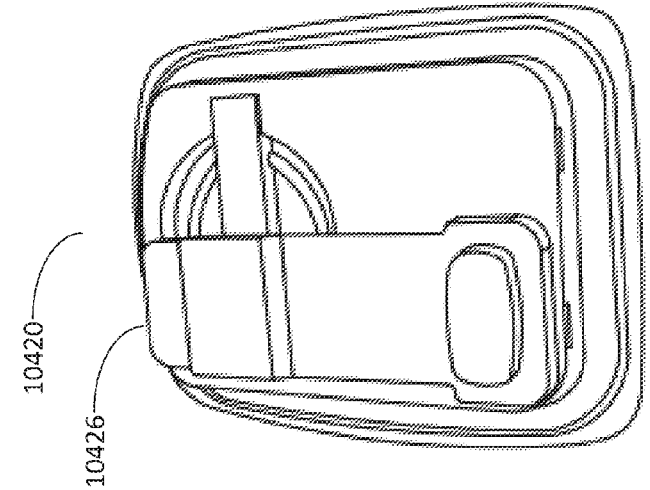
FIG. 16A illustrates a line diagram depicting slider for low intake of air, in accordance with an embodiment of the invention.

Now referring to FIG. 16A-16C, illustrates the multiple positioning of the slider unit 10426 on the airflow vent 10420. FIG. 16A displays low oxygen intake level. At this level, there is very minimal intake of air and thus Oxygen. FIG. 16B illustrates medium oxygen intake level. At this position, the intake of Oxygen is at a medium level. Further, FIG. 16C, illustrates high intake level that is the highest possible opening of the airflow vent 10420. At this level, the slider unit 10426 is at the extreme right position. It should be understood, POSITA can generate various other intermediate levels. The levels described above are exemplary and can be modified. It is to be noted that the air inflow restriction control does not interfere too much with air outflow control.

Aspects of the present subject matter are described herein with reference to flowchart illustrations and/or block diagrams of methods and apparatus (systems) according to embodiments of the subject matter. It will be understood that each block of the flowchart illustrations and/or block diagrams, and combinations of blocks in the flowchart illustrations and/or block diagrams, can be implemented by computer readable program instructions.

While there has been shown, and described herein what are presently considered the preferred embodiments of the present disclosure, it will be apparent to those skilled in the art that various changes and modifications can be made therein without departing from the scope of the present disclosure as defined by the appended claims.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While certain embodiments have been described, these embodiments have been presented by way of example only, and are not intended to limit the scope of the present disclosure. Indeed, the novel methods, devices, and systems described herein may be embodied in a variety of other forms. Furthermore, various omissions, substitutions, and changes in the form of the methods, devices, and systems described herein may be made without departing from the spirit of the present disclosure. The accompanying claims and their equivalents are intended to cover such forms or modifications as would fall within the scope and spirit of the present disclosure.

What is claimed is:

1. A sports mask comprising:
    a head band assembly configured to hold the sports mask to head of a user while the sports mask is in use; and
    a face mask unit to cover a mouth and nose region of the user, the face mask comprising
        an outer unit, the outer unit being an individual standalone module,
        an inner most unit, the inner most unit being an individual standalone module separate from the outer unit, and
        a middle unit, the middle unit being an individual standalone module separate from the outer unit and the inner most unit, wherein the middle unit is received between the outer unit and the inner most unit to be assembled together to obtain the face mask unit,
        each of the outer unit, the middle unit and the inner most unit having a cavity adapted to be located concentrically as the outer unit, the middle unit and the inner most unit being assembled together, wherein the outer, middle and inner most units are in decreasing order of sizes thereof and complements each other in shape to be snugly assembled together,
    a face band assembly extending from the face mask unit and coupled to the head band assembly to hold the face mask unit to cover the mouth and nose region of the user,
    a grill cover coupled to the outer unit, the grill cover having an opening, wherein the opening is located concentrically to the cavities,
    a grill adapted to be received by the opening of the grill cover, and
    a modular air flow valve assembly adapted to be received by the cavity of the inner most unit to enable the air flow valve assembly to be in communication with the grill, the modular air flow valve assembly comprising,
        an airflow vent, the airflow vent having a first cutout, and a second cutout configured below the first cutout and extending only up to half a portion of the first cutout, each of the first and second cutouts having air holes,
        an airflow valve adapted to be disposed over the first cutout of the airflow vent, the first cutout including a pair of valve catcher notches configured linearly across each other,
        a valve catcher adapted be placed over the airflow valve and distal ends of the valve catcher are engaged with the pair of valve catcher notches to place the airflow valve in the engaging position with the airflow vent, and
        a slider unit adapted to engage with the valve catcher along the first cutout and adapted to extend up to an entire region of the second cutout to cover the air holes of the second cutout, the slider unit to slide linearly over the valve catcher to open and close the air holes of the second cutout, the slider unit adapted to be shifted to multiple positioning to generate various intermediate levels between a minimum and a maximum opening levels of the second cutout to vary flow of air flowing in the air flow valve assembly from the second cutout.

2. The sports mask of claim 1, wherein the face band assembly comprises a left strap and a right strap, each extending from the outer unit of the face mask unit.

3. The sports mask of claim 2, wherein the head band assembly comprises a left clip to receive the left strap and a right clip to receive the right strap of the face band assembly.

4. The sports mask of claim 3, wherein the left strap and the right strap are releasably attached to the left clip and the right clip, respectively.

5. The sports mask of claim 4, further comprising a fastener at ends of the left strap and the right strap to releasably attach with the left clip and the right clip, respectively.

6. The sports mask of claim 1, wherein the slider unit being a longitudinal structure, and comprises:
   a sliding notch through which the sliding unit is slidably affixed to the valve catcher to slid over the valve catcher; and
   a sliding button coupled to the sliding unit to be pushed to enable linear movement of the sliding unit, through the sliding notch, over the valve catcher to open and close the air holes of the second cutout to vary flow of air flowing from the grill in the air flow valve assembly, wherein the sliding notch and the sliding button being configured along opposite to each other at distal end portions of the slider unit.

7. The sports mask of claim 6, wherein the slider unit further comprises a motor to automatically push the sliding button to facilitate linear sliding movement of the slider unit, through the sliding notch, over the valve catcher to open and close air holes of the second cutout to vary flow of air flowing from the grill in the air flow valve assembly.

8. The sports mask of claim 7, further comprising:
   a vital parameter collection device attached to the innermost unit of the face mask, the vital parameter collection device adapted to collect and monitor data related to requirement of oxygen to the user; and
   a microcontroller embedded within the face assembly, and, in direct communication with the vital parameter collection device, the microcontroller, as per requirement of oxygen, may control the sliding of the slider unit by controlling the motor.

9. The sports mask of claim 6, wherein the sliding button is manually pushed by the user to facilitate linear sliding movement of the slider unit, through the sliding notch, over the valve catcher to open and close air holes of the second cutout to vary flow of air flowing from the grill in the air flow valve assembly.

10. The sports mask of claim 1, wherein the grill comprises:
    a frame with a frame base, the frame, through the frame base, secured in the opening of the grill cover to couple the grill with the grill cover; and
    a plurality of fines disposed along the frame to filter the air passing there-through.

11. The sports mask of claim 1 further comprising:
    a button electronically embedded in the sports mask to wirelessly couple the sports mask to an external device.

12. A system for monitoring oxygen level in a user, the system comprising:
    a sports mask comprising,
        a head band assembly configured to hold the sports mask to head of a user while the sports mask is in use; and
        a face mask assembly having,
            a face mask unit to cover a mouth and nose region of the user, the face mask comprising
                an outer unit, the outer unit being an individual standalone module,
                an inner most unit, the inner most unit being an individual standalone module separate from the outer unit, and
                a middle unit, the middle unit being an individual standalone module separate from the outer unit and the inner most unit, wherein the middle unit is received between the outer unit and the inner most unit to be assembled together to obtain the face mask unit,
                each of the outer unit, the middle unit and the inner most unit having a cavity adapted to be located concentrically as the outer unit, the middle unit and the inner most unit being assembled together, wherein the outer, middle and inner most units are in decreasing order of sizes thereof and complements each other in shape to be snugly assembled together,
            a face band assembly extending from the outer unit of the face mask unit and coupled to the head band assembly to hold the face mask assembly to cover the mouth and nose region of the user,
        a grill cover coupled to the outer unit, the grill cover having an opening, wherein the opening is located concentrically to the cavities,
        a grill adapted to be received by the opening of the grill cover, and
        a modular air flow valve assembly to be received by the cavity of the inner most unit to enable the air flow valve assembly to be in communication with the grill, the modular air flow valve assembly comprising,
            an airflow vent, the airflow vent having a first cutout, and a second cutout configured below the first cutout and extending only up to half a portion of the first cutout, each of the first and second cutouts having air holes,
            an airflow valve adapted to be disposed over the first cutout of the airflow vent, the first cutout including a pair of valve catcher notches configured linearly across each other,
            a valve catcher adapted be placed over the airflow valve and distal ends of the valve catcher are engaged with the pair of valve catcher notches to place the airflow valve in the engaging position with the airflow vent, and
            a slider unit adapted to engage with the valve catcher along the first cutout and adapted to extend up to an entire region of the second cutout to cover the air holes in the second cutout, the slider unit to slide linearly over the valve catcher to open and close the air holes of the second cutout, the slider unit adapted to be shifted to multiple positioning to generate various intermediate levels between a minimum and a maximum opening levels of the second cutout to vary flow of air flowing in the air flow valve assembly from the second cutout; and
    a wearable device wirelessly connected to the sports mask, the wearable device having monitoring function to control the air flow resistance varying module to vary flow of air flowing from the grill in the air flow valve assembly.

13. The system of claim 11 further comprising:
- a vital parameter collection device attached to the innermost unit of the face mask, the vital parameter collection device adapted to collect and monitor data related to requirement of oxygen to the user and send the same to the wearable device; and
- a microcontroller embedded within the face assembly, and, in communication with the vital parameter collection device and the wearable device, the microcontroller, as per requirement of oxygen to the user, may control the air flow resistance varying module, by controlling a motor, based on instruction of the wearable device.

* * * * *